(12) United States Patent
Deister

(10) Patent No.: US 11,589,870 B2
(45) Date of Patent: Feb. 28, 2023

(54) IMPLANT DEVICES WITH A PRE-SET PULLEY SYSTEM

(71) Applicant: Axogen Corporation, Alachua, FL (US)

(72) Inventor: Curt Deister, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 246 days.

(21) Appl. No.: 17/159,460

(22) Filed: Jan. 27, 2021

(65) Prior Publication Data

US 2021/0307753 A1 Oct. 7, 2021

Related U.S. Application Data

(63) Continuation of application No. 15/252,917, filed on Aug. 31, 2016, now Pat. No. 10,945,737.

(Continued)

(51) Int. Cl.
*A61B 17/11* (2006.01)
*A61B 17/04* (2006.01)

(52) U.S. Cl.
CPC ...... *A61B 17/1128* (2013.01); *A61B 17/0487* (2013.01); *A61B 17/0466* (2013.01); *A61B 2017/0417* (2013.01); *A61B 2017/0475* (2013.01); *A61B 2017/0477* (2013.01); *A61B 2017/0496* (2013.01); *A61B 2017/1132* (2013.01); *A61B 2017/1142* (2013.01)

(58) Field of Classification Search
CPC ........... A61B 17/1128; A61B 17/0401; A61B 2017/00004; A61B 2017/0417;

(Continued)

(56) References Cited

U.S. PATENT DOCUMENTS 4,400,833 A 8/1983 Kurland
4,778,467 A 10/1988 Stensaas et al.
(Continued)

FOREIGN PATENT DOCUMENTS

JP 2011025034 2/2011
WO WO 2007/037326 4/2007

OTHER PUBLICATIONS

Japanese Notice of Reasons for Rejection in corresponding Japanese Application No. 2018-542122, dated Aug. 12, 2020 (12 pages).

(Continued)

*Primary Examiner* — Timothy J Neal
*Assistant Examiner* — Andrew P. Restaino
(74) *Attorney, Agent, or Firm* — Bookoff McAndrews, PLLC

(57) ABSTRACT

The problem of positioning one or more nerve ends inside a sheathing implant is solved by the use of a pulley and cinching systems that pull a nerve end into an implant and that can adjust the diameter of an implant to conform the implant to the diameter of the nerve, respectively. The pulley system utilizes a suture that traverses the wall of an implant leaving one end outside the implant wall and another end that can be attached to a nerve. Pulling the suture end outside the wall pulls the nerve attached to the other end of the suture into the bore of the implant. A cinching system utilizes specially arranged sutures within the wall of an implant to tighten or cinch up the wall after a nerve is placed therein, so as to conform at least part of the implant to the diameter of the nerve. Methods are also disclosed by which such pulley systems can be formed during an intraoperative procedure.

28 Claims, 14 Drawing Sheets

Related U.S. Application Data

(60) Provisional application No. 62/247,938, filed on Oct. 29, 2015.

(58) Field of Classification Search
CPC ........ A61B 2017/0464; A61B 17/1114; A61B 17/1146; A61B 17/11; A61B 2017/1107; A61B 2017/1132; A61B 2017/1135; A61B 2017/1139; A61B 2017/081; A61B 2017/1103; A61F 2002/087; A61F 2/0063; A61F 2/08; A61F 2/0811
See application file for complete search history.

(56) References Cited

U.S. PATENT DOCUMENTS

| | | |
|---|---|---|
| 5,147,399 A | 9/1992 | Dellon et al. |
| 6,102,921 A | 8/2000 | Zhu et al. |
| 6,749,616 B1 | 6/2004 | Nath |
| 8,257,365 B2 | 9/2012 | Demarais et al. |
| 9,629,997 B2 | 4/2017 | Desiter et al. |
| 2003/0130694 A1 | 7/2003 | Bojarski et al. |
| 2005/0038471 A1 | 2/2005 | Chan et al. |
| 2009/0131980 A1 | 5/2009 | Wiesman et al. |
| 2012/0209318 A1 | 8/2012 | Qadeer |
| 2013/0123810 A1 | 5/2013 | Brown et al. |
| 2014/0379009 A1 | 12/2014 | Yu et al. |
| 2015/0173739 A1 | 6/2015 | Rodriguez et al. |
| 2016/0331511 A1 | 11/2016 | Kassab |

OTHER PUBLICATIONS

Communication pursuant to Article 94(3) issued in counterpart European Patent Application No. 16196659.9 dated Feb. 15, 2019, 5 pages.

International Search Report issued in PCT Application Serial No. PCT/US2016/049660 dated Dec. 8, 2016, 15 pages.

Extended EP Search Report issued in EP Application Serial No. 16196656.9 dated Feb. 21, 2017, 7 pages.

• CINCH PULLED TIGHT RESULTING IN BETTER FIT OF CONDUIT

FRONT VIEW

BACK VIEW

1 ARM ATTACHED TO NERVE

ALL ARMS ATTACHED TO NERVE (8 TOTAL; 4 PULLEYS)

2 PULLEYS DRAWN IN AND TIED OFF (FRONT)

ALL PULLEYS DRAWN IN AND TIED OFF

IMPLANT DEVICES WITH A PRE-SET PULLEY SYSTEM

CROSS-REFERENCE TO RELATED APPLICATIONS

This application is a continuation of U.S. patent application Ser. No. 15/252,917, filed Aug. 31, 2016, which claims the benefit of U.S. provisional application Ser. No. 62/247,938, filed Oct. 29, 2015, all of which are incorporated herein by reference in their entireties.

This invention was made with government support under contract no. W81XWH-13-1-0448 awarded by the Department of Defense. The government has certain rights in the invention.

BACKGROUND OF INVENTION

After a nerve injury, direct coaptation of the nerve ends provides the most favorable results for nerve regeneration. Successful nerve regeneration can be further promoted if the coaptation site or neurorraphy line is separated and isolated from the surrounding tissues, which can inhibit the formation of scar tissue and neuromas. Neuromas often result from nerve fibers or neurons that improperly and irregularly grow into the surrounding tissue. In situations where a nerve is not, or cannot, be repaired, there can be left a nerve stump that must be isolated or covered to minimize or inhibit the formation of painful scar tissue and neuromas, which can cause debilitating pain and, in some instances, even limit or prevent the use of a prosthesis.

There are several techniques by which the coaptation site or a nerve stump can be isolated, including the use of a nerve sheath implant, such as a sleeve or cap, into which the nerve ends or the nerve stump, respectively, can be inserted and secured with sutures. The material utilized for a nerve sheath implant should be flexible and capable of being sutured, so that it can be conformed around the nerve to further discourage neuronal outgrowth into the surrounding tissue.

With nerve coaptation, regeneration is most favorable when the nerve ends are aligned in a nerve repair sleeve so that faces are directed at each other with minimal bunching or deformation. Likewise, nerve stumps often heal more effectively if the nerve face is directed fully into the nerve repair cap and does not fold or bunch-up, which can undesirably encourage nerve fibers to grow out of the cap instead of towards the end of the cap. These configurations can be difficult to achieve when pushing, poking, or otherwise trying to manipulate soft nerve tissue into the aperture, or open end, of a nerve sheath implant.

This problem can be partly resolved by utilizing a cap or sleeve that is oversized for the nerve ends being covered. This leaves the necessity, however, of having to meticulously suture the sleeve or cap to the outside of the nerve to reduce diameter and ensure that the nerve ends are sufficiently isolated and separated to discourage neuronal outgrowth into the surrounding tissue.

It is well-understood that every puncture, or suture, made within the epineurium or nerve sheath increases the opportunity for neuronal escape and can potentially increase time of healing. Thus, the difficulty of inserting nerve ends into a properly sized sleeve or cap must be weighed against the necessity of having to use additional sutures to secure an oversized sleeve or cap.

BRIEF SUMMARY

In accordance with embodiments of the subject invention, the difficulty of inserting a nerve end into a nerve sleeve, nerve cap, or other similarly-used sheathing implant device is addressed by fashioning such nerve sheath devices with pre-set suture pulley systems that can, in one embodiment, be attached to a nerve end and used to pull the nerve end through the aperture, or open end, and into the bore of the implant and in other embodiments can be used to tighten or cinch the aperture and/or bore of an oversized sheath implant around the periphery of a nerve.

The subject invention addresses the disadvantages associated with the previously known nerve sheaths, such as nerve sleeve and nerve cap devices, and their methods of use, and provides attributes and advantages that have not been realized by those known devices. In particular, the subject invention provides novel, inexpensive, and highly effective improvements to currently known implant devices used to separate and isolate nerve ends and coaptation sites.

Certain embodiments of a pre-set pulley system can be used to cinch an oversized sheath implant, so as to tighten it around a smaller diameter nerve. This tightening pulley system can have a suture, thread, line, or other flexible elongated material arranged in a specific configuration that traverses through specific points on the sheath implant device. Once a nerve end or nerve ends have been placed within the bore of the implant device, one or more of the lines can be pulled to decrease the diameter (D) of the implant and cinch the bore walls and the aperture around the nerve end or nerve ends.

Other embodiments of a pre-set pulley system can be used to pull or draw the nerve ends into the sheath implant device, so that they come together properly, with minimal bending, crimping, or distortion of the facing end. When coapting two nerve ends within an implant device, such as a nerve sleeve, the facing ends can be properly aligned and spaced using this coapting pulling system. If drawing one nerve end into a nerve cap, the facing end can be fully directed towards the closed end of the nerve cap, to minimize incorrect neuronal growth. This coapting pulley system can position nerve ends more advantageously within the sheath implant device, which can facilitate better and faster healing. With this system, at least one, ideally at least two, sutures, or similar type of device is passed through the wall of a nerve sleeve or nerve cap, so that the tag end of the suture is outside of the implant device bore and the other, needle end, goes through the bore and out of one of the apertures. The needle end can be passed through a nerve, or at least the epineurium, and secured by knotting followed by removal of the needle. The free tag end, outside the bore, can then be pulled away from the bore, which simultaneously draws or pulls the nerve end at the other end of the suture line through the aperture and into the bore.

Variations or combinations of both of these types of pulley systems can be used with nerve repair sleeves and nerve repair caps implanted in patients in need of such treatment. While the use of the pulley systems can require one or more additional sutures at the nerve end, which has the potential to further damage neurons already in need of repair, it can reduce the number of sutures needed around the aperture to secure the implant device to the nerve. Thus, nerve healing could still be faster or at least no more inhibited by the use of the pulley system. In the case of a nerve stump, neuronal damage at the nerve end is often of minor concern, since reduction in neuronal growth is typically the purpose of utilizing a nerve repair cap.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings.

FIG. 5A shows an embodiment where a single cinching loop is used nearer to an open end(s) of an implant. When the cinching loop is pulled, the apertures are reduced in size and a pucker is formed in the wall at either open end of the implant and the effective diameter of the implant is reduced. In FIG. 5B there is shown a single suture line threaded through one side of the implant wall multiple times to create more than one cinching loop, where at least one can be pulled to cinch up the apertures as well as the diameter of the implant.

DETAILED DISCLOSURE

Figure 1:
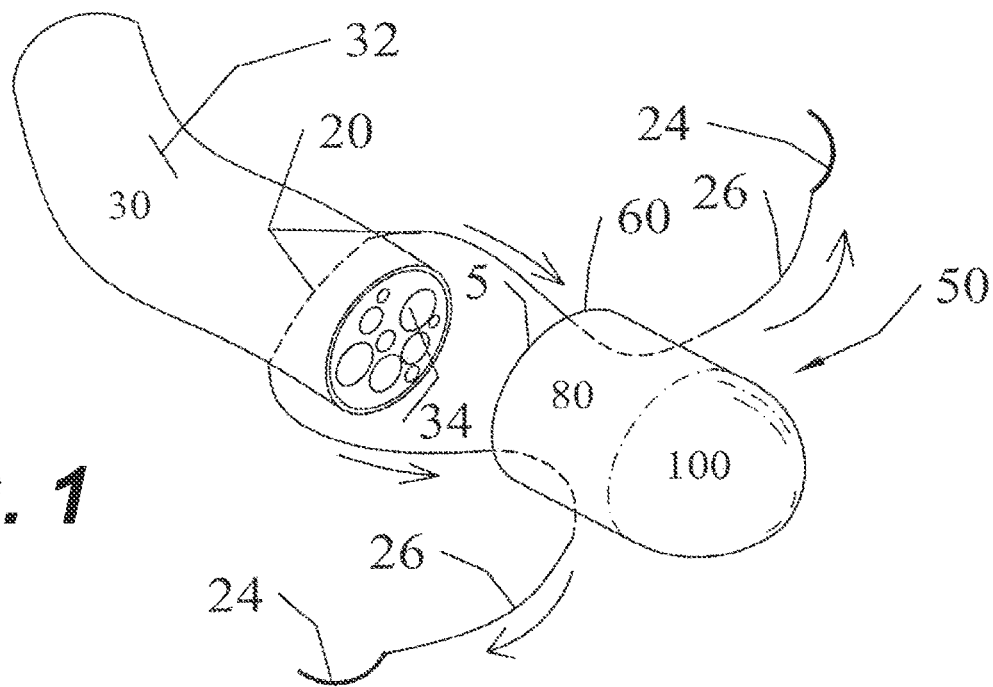
FIG. 1 illustrates one embodiment of a sheathing implant nerve cap pre-set with a suture pulley system for dragging a nerve end into the nerve cap. With this embodiment of a nerve cap pulley system, a single suture line is used to traverse both the nerve end and the wall of the cap.

The subject invention pertains to embodiments of a sheathing implant, such as a nerve sleeve, nerve cap, or similar type of flexible implant capable of positioning and isolating nerve ends to facilitate nerve repair or prevent/isolate end bulb neuromas. More specifically, the subject invention provides sheathing implants capable of being used to coapt nerves to each other or to such sheathing implant. In particular there are provided sheathing implants with one or more suture pulley systems that can be used to attach to a nerve end and pull or draw the nerve end into the implant. Other embodiments provide nerve repair sheathing implants with a cinching loop that can be used to conform an implant to the shape and/or size of a nerve therein. These pulley systems can be used independently or in various combinations to effect a safe, secure, easy nerve repair in patients in need of such treatment.

The subject invention is particularly useful in the field of nerve repair, in particular implantable sheathing devices used in the treatment of nerve repair. However, a person with skill in the art will be able to recognize numerous other uses that would be applicable to use with the devices and methods of the subject invention. While the subject application describes, and many of the terms herein relate to, a use for nerve repair and implants used therefor, other modifications apparent to a person with skill in the art and having benefit of the subject disclosure are contemplated to be within the scope of the present invention. By way of non-limiting example, uses for tendon, blood vessel, intestine, or muscle repair are contemplated to be within the scope of the subject invention. Thus, reference herein to a nerve or nerve end should not be construed as limiting the subject invention.

In order to provide a clear and consistent understanding of the specification and claims, including the scope to be given such terms, the following definitions are provided.

The term "patient" as used herein, describes any animal, including mammals, to which the devices and methods of the present invention can be applied and which is in need of such treatment.

The term "surgeon" as used herein is merely for literary convenience. The term should not be construed as limiting in any way. The devices, apparatuses, methods, techniques and/or procedures of the subject invention could be utilized by any person desiring or needing to do so and having the necessary skill and understanding of the invention.

The terms "sheathing implant" or "implant" are also used herein for literary convenience. These terms as used refer to any type of implantable device, usually tubular, in which tissues are emplaced or coapted to facilitate isolation and/or repair. This can include, but is not limited to, nerve caps that are placed over the end of a nerve stump or nerve sheaths or nerve sleeves in which two nerve ends are inserted or wrapped. While the subject application is written towards tubular shaped nerve sheath implants, the devices and techniques described herein are not limited to just nerve repair devices.

Furthermore, a sheathing implant useful with the embodiments and techniques of the subject invention is not limited to a particular type of material. Preferably, an implant can be made of a biocompatible material, and while it can be, it does not necessarily have to be, a biodegradable material or other material capable of tissue remodeling. For example, both natural and synthetic biomaterials can be used to manufacture a sheathing implant of the subject invention. In certain embodiments, the biomaterial is a homogenous material. Examples of biomaterials for use in manufacturing the subject invention include, but are not limited to, high density polyethylene (HDPE), polyethylene glycol (PEG) hydrogel, purified proteins from human or animal sources (e.g., membrane of purified collagen or fibrin), and decellularized tissue constructs (e.g., demineralized bone, amnion, SIS, deaths, or fascia). An HDPE or PEG device can comprise or consist of a cylinder of porous HDPE or PEG surrounded by a layer of non-porous HDPE or PEG. Biomaterials that can form a fluid material, such as soluble purified collagen or particulate SIS and dermis, can be directly cast to form the device without a membrane as an intermediate.

In addition, references to "first", "second", and the like (e.g., first and second aperture), as used herein, and unless otherwise specifically stated, are intended to identify a particular feature of which there can be at least two. Such reference herein to "first" does not imply that there must be two or more. Furthermore, these references are not intended to confer any order in time, structural orientation, or sidedness (e.g., left or right) with respect to a particular feature.

Finally, reference is made throughout the application to an "open end" and a "closed end." As used herein, an open end is that end of the device that is uncovered and has an aperture or edge through which a tissue, such as a nerve end, can be drawn or pulled into a sheathing implant. Conversely, a closed end is that end often furthest from the open end or that portion or area of a sheathing implant where the end or face of the tissue to be covered or coapted is situated after being drawn or pulled into the implant. A closed end can be capped so that the implant is a blind hole or, alternatively, it can be an area in the implant where the nerve tissue is completely covered by the walls of the device, which can be, but is not required to be at or near the center of the implant.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the subject invention, it can be seen that the embodiments of an sheathing implant 50 of the subject invention are generally tubular or can be made tubular, such as in the case of pre-rolled wrapping implants, and include at least one aperture 60, at an open end 5 through which a tissue can pass, such as, for example, a nerve end that leads to at least one bore 70 defined by a wall 80 in which the tissue, after passing through the aperture, can reside at or near to a closed end 10. Certain embodiments also include a cap 100 at the closed end for isolating a tissue that is not to be coapted to another tissue. The sheathing implant embodiments herein also include at least one of a pulley system 200 that can be used to draw a tissue into the bore and a cinching loop 300 that can be used to tighten a sheathing implant around a nerve end or other tissue. Each of these general components can have one or more sub-components, which will be discussed in detail below.

The process of placing a nerve end into a tubular sheathing implant can entail pushing, probing, rotating, or otherwise getting the nerve end through an aperture 60 in the implant. This can be tedious, time-consuming, and can damage the nerve 30 or the nerve face 34 or possibly the implant 50. The pulley system 200 embodiments of the subject invention provide sheathing implants and methods that can be incorporated with sheathing implants and used to pull a nerve 30 through the aperture of an implant with minimal or no pushing or probing of the nerve end. The cinching loop 300 embodiments of the subject invention can also be incorporated with sheathing implants and used to tighten the implant around the epineurium 32 or external covering of the nerve 30. A pulley system and a cinching loop can be used individually or together on a sheathing implant.

In general, a pulley system embodiment utilizes at least one suture 20 that has been pre-set in an implant. The pre-set suture can go through or traverse the implant wall 80 that defines the bore 70 of the implant, so that a needle end 24 of the suture goes through the bore and extends out of the aperture and the opposite end or tag end 26 of the suture extends out from the side of the wall. The needle end can then be used to attach the at least one suture to a nerve end by means of a knot. Once the nerve end has been attached to the suture and the needle removed, the tag end on the outside of the implant wall can be pulled, which in turn pulls the end of the nerve through the aperture and into the bore of the implant. If the suture is attached near to the nerve face 34, the nerve face will be located approximately where the suture extends out of the wall. Variations of the pulley system can have a single suture that goes through the nerve and traverses the implant wall in two locations or have a single suture that traverses through one side of the wall so that a pulley loop 230 is formed that can be pulled to simultaneously draw or pull two nerves into opposite apertures in a sheathing implant.

A cinching loop embodiment, in general, utilizes at least one suture 20 that has been pre-set in an implant wall. The pre-set suture can go through or traverse the implant wall 80 in at least two or more locations, so that in one embodiment one end is secured outside the wall or so that a portion of the suture forms a stitch 310 parallel to the bore on the outside of the wall. The one or two tag ends of the suture line extend through one side of the bore and out through the wall on the other side of the bore, leaving one or two tag ends 26 of the suture dangling outside the wall opposite to the anchored end or the stitch. The suture tag ends extending out from the wall can be used separately or they can be attached to form a noose knot 315 that, when one suture is pulled away from the implant wall causes the suture line to tighten, pulling the stitch and bringing opposing sides of the wall together, thereby reducing the diameter of the bore and/or the aperture by creating a pucker 320 in the wall. In other words, the implant wall can be cinched up with a suture to tighten it around a nerve in the bore.

Figure 2:
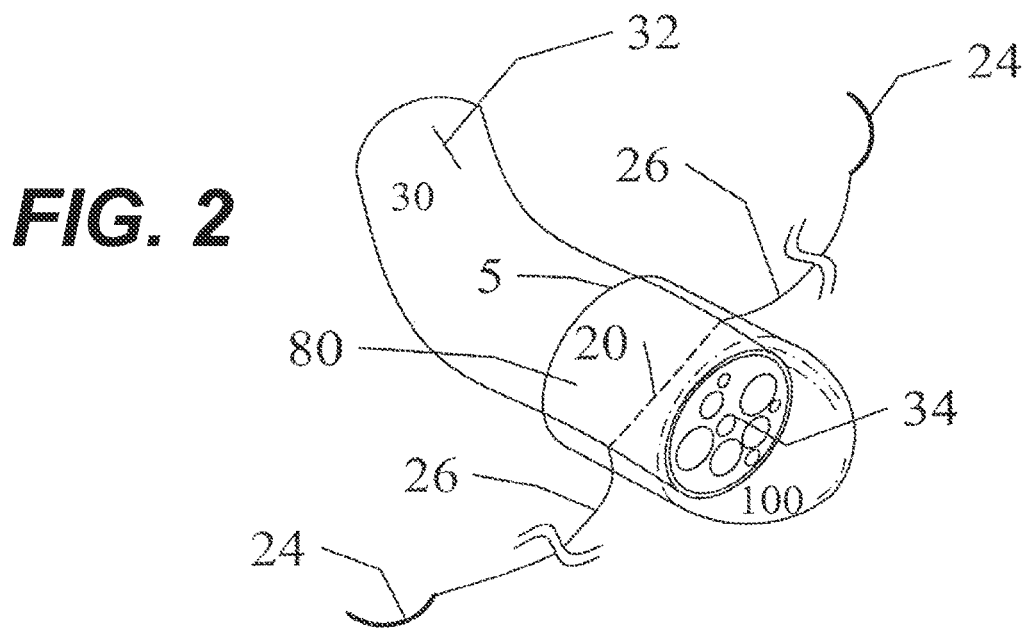
FIG. 2 illustrates how the two tag ends of a single suture line of a nerve cap pulley system can be pulled apart to draw tight the suture and to bring a nerve end inside the nerve cap of FIG. 1.
Figure 3:
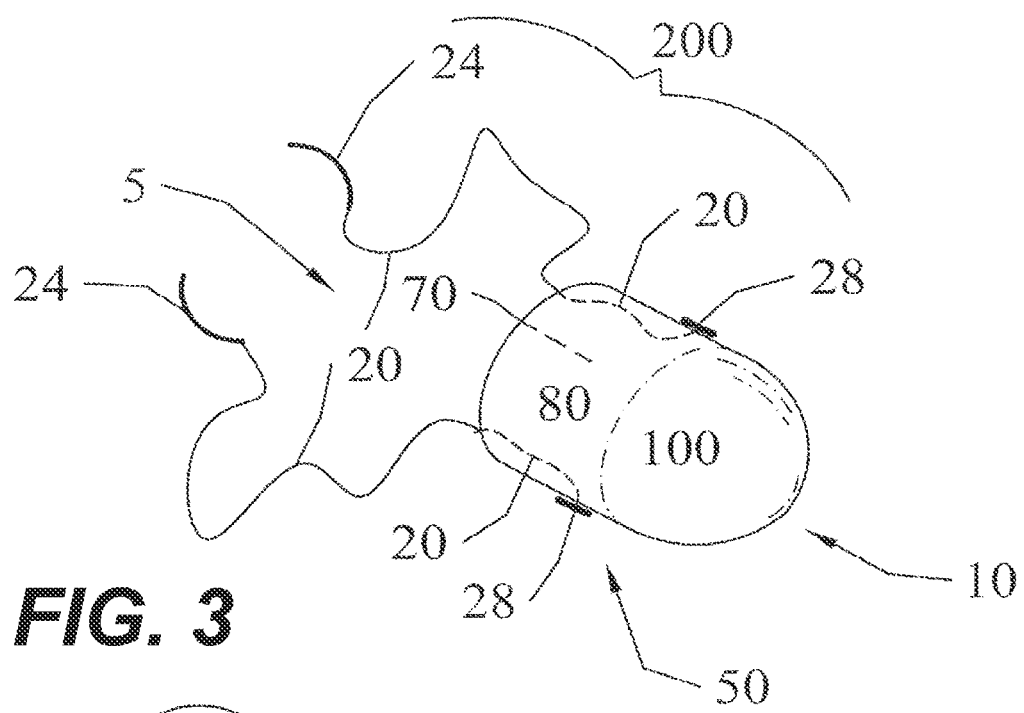
FIG. 3 illustrates an alternative embodiment of a nerve cap pre-set with a suture pulley system for dragging a nerve end into a nerve cap. With this embodiment of a nerve cap pulley system, two or more suture lines can be used to traverse both the wall of the cap and attach to the nerve end. When the free tag ends of the two or more suture lines outside the wall of the implant are drawn tight, the nerve end can be drawn into the nerve cap.

In one embodiment, an implant is pre-set with a single suture line. FIGS. 1 and 2 illustrate an embodiment of a nerve cap having an aperture 60 at one end and a cap 100 at the opposite end, which forms a "blind hole" for a nerve end. A single suture line can be arranged to traverse the implant wall in two, generally opposite, positions with the nerve end also attached therebetween, as shown in FIG. 1. With this embodiment, a suture can be pre-set traversing the implant wall in a first location, so that the needle end 24 passes through the bore and out of the aperture, leaving a suture tag end 26 dangling outside the wall 80. Alternatively, the can be secured with an anchor 28, which can be a knot in the tag end or another device or structure to which the tag end is attached, an example of which is shown in FIG. 3. The needle end can then be used to pass the suture through the nerve. The needle end can further be passed back through the implant wall at a second location from within the bore, so that the needle end extends out from the wall approximately opposite to the tag end on the other side of the wall. This creates two opposing tag ends 26 extending out from the implant wall and the nerve attached therebetween, again, as shown in FIG. 1. When the two suture tag ends 26 are pulled, for example, in opposite directions, the shortening of the suture between the wall locations pulls the nerve through the aperture 60 and into the bore 70 of the implant 50, as shown, for example, in FIG. 2. In a nerve cap implant, this process can place the nerve face 34 against or facing the cap 100. If necessary, the nerve end can be guided or helped into the aperture using the fingers or surgical tools to manipulate the edges through the aperture. But, the main impetus of force drawing the nerve into the implant can be the pulling of the suture line.

Figure 4:
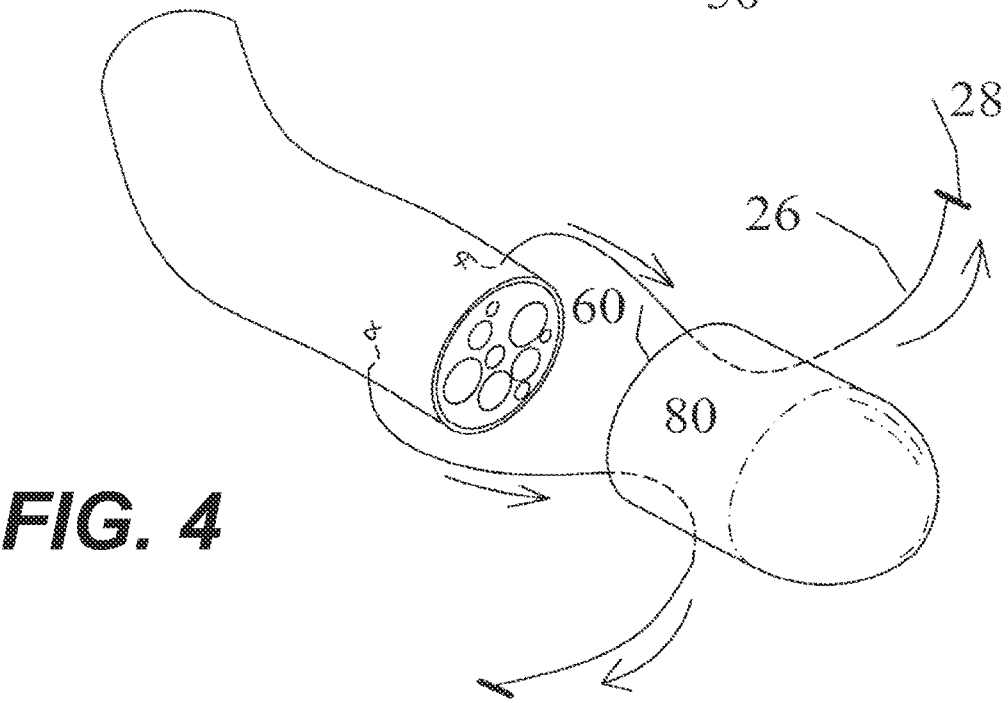
FIG. 4 illustrates the alternative embodiment of a nerve cap pulley system in FIG. 3 after it is attached to a nerve end, so the tags of the two or more suture lines can be pulled away from the cap wall so as to drag the nerve end through the aperture and into the bore of the cap.

An alternative embodiment utilizes two sutures, each configured with a needle end 24, and each needle end traversing the wall so that the opposite end or tag end 26 is extending out from the wall 80 and the needle ends extend out of the aperture. FIGS. 3 and 4 illustrate an example of a nerve cap implant that utilizes this type of pulley system 200 embodiment. In FIG. 3 it can be seen that at least two suture lines can be passed through the wall 80 at approximately, but not necessarily, opposite sides. The needle ends 24 can pass through the bore 70 and out of the aperture 60. The embodiment shown in FIGS. 3 and 4 have the tag tag ends secured with anchors 28 that can prevent the tag ends from being accidentally pulled through the wall into the bore. However, the tag ends could be unsecured or dangle freely, as seen in FIGS. 1 and 2. The needle ends can be passed through a nerve and secured with knots, so that the needle portion is removed. As above, the tag ends can then be pulled away from the wall to draw or pull the nerve through the aperture and into the bore, usually until the nerve face 34 is even, or approximately even, with points where the tag ends exit the bore.

Tissue sheathing implants 50 are not limited to those with a capped end 100. Others, often referred to as sleeve implants 150, are designed to cover and protect two coapted nerve ends to facilitate healing. With these types of sheathing implants there can be two open ends with apertures that lead into a central, continuous bore. Nerve ends are placed through the apertures and pushed into the bore towards each other and the closed end or covered portion until their faces are sufficiently close. The aperture is then sutured around the nerve epineurium 32 to hold the sleeve implant and the nerve ends in place.

A pulley system 200 can also be utilized with a sleeve implant 150 having two apertures. In one embodiment, two needle end sutures can be pre-set within a nerve sheath. The needle ends of each suture can each extend through the bore 70 and out of an aperture 60, such that there are needle ends extending from the aperture at each end of the sleeve implant. Some portion of the suture can traverse the implant wall 80 near the closed end so that tag ends 26 are formed on the outside of the implant sheath, as shown, for example, in FIG. 11. In an alternative embodiment, the tag ends can be joined to form a pulley loop 230 on the outside of the wall 80, which is shown, for example, in FIG. 12.

Figure 11:
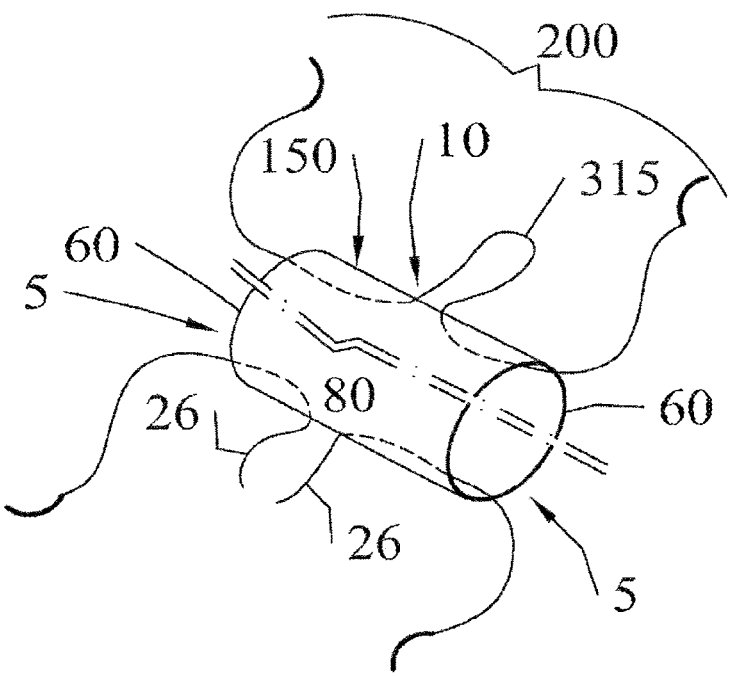
FIG. 11 is an illustration of two embodiments of a multi-pulley system for a nerve sleeve. With this embodiment, at least one suture can be threaded through the implant wall from one aperture to the other aperture of a nerve sleeve so that a pulley loop is formed at about the center of the nerve sleeve, which can be used to draw the ends of the nerves into each aperture, as shown at the top of the figure. Alternatively, two separate sutures can traverse the wall so the needle ends extend towards the open end from each aperture and the tag of each suture extends from the wall of the implant.
Figure 17:
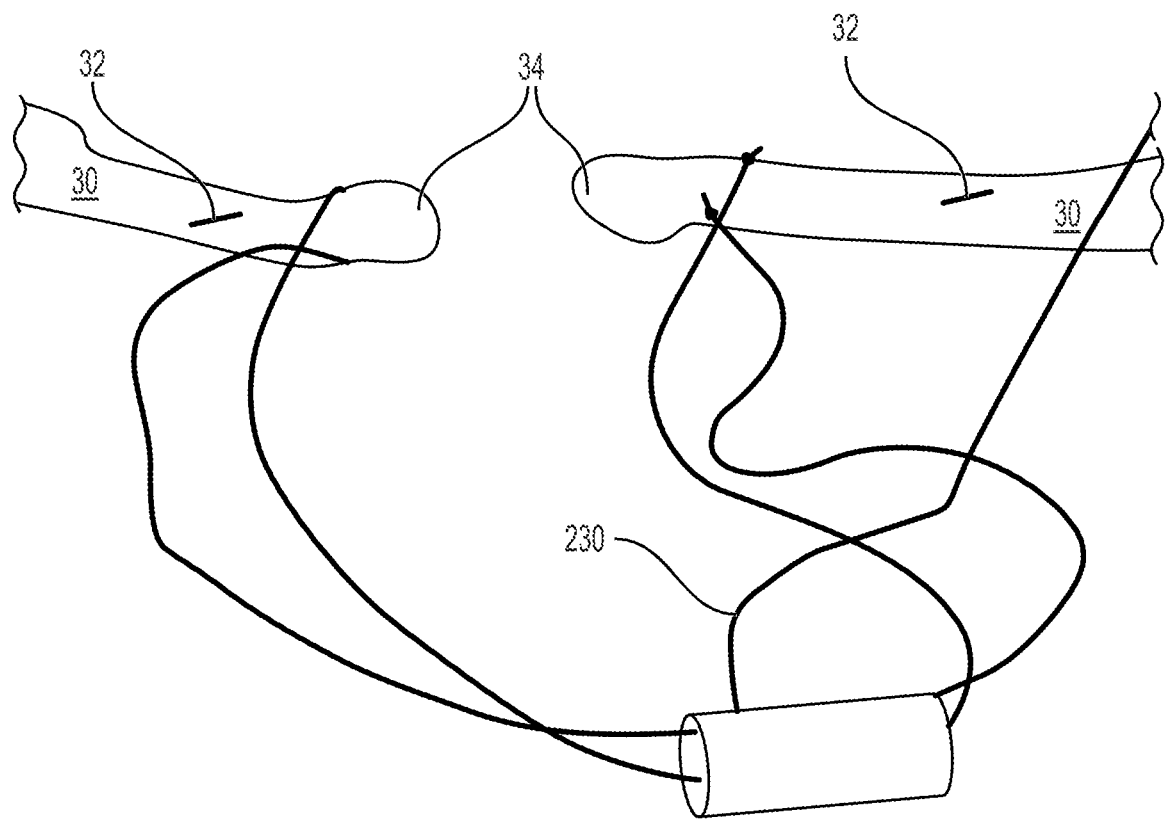
FIG. 17 is a photograph showing the sutures of a multi-pulley system for a nerve sleeve being attached to the ends of a nerve and to the wall of an implant. The four suture tags are placed into the epineurium of the nerve stumps and secured. A cinching loop has also been incorporated with the implant, which is shown here as the knotted loop on the right side of the photograph.

In one embodiment, the needle end of at least two sutures can be passed through the wall leaving tag ends 26 extending out of the wall 80 near the closed end 10 and the needle ends can pass through the bore and out of each aperture 60 for attachment to nerve ends. FIG. 11 illustrates an example of this configuration, where one side of the sleeve implant 150 is shown with two tag ends and two needle ends. The alternative embodiment with a pulley loop 230 can be formed by either tying the tag ends 26 together outside of the sleeve wall to form a pulley loop, one example of which is shown in FIG. 17, or passing one of the needle ends of a dual needle suture through the wall twice to form a pulley loop outside the wall and at or near the closed end 10, which is shown, by way of example, on the other side of the sleeve wall in FIG. 11.

Figure 12:
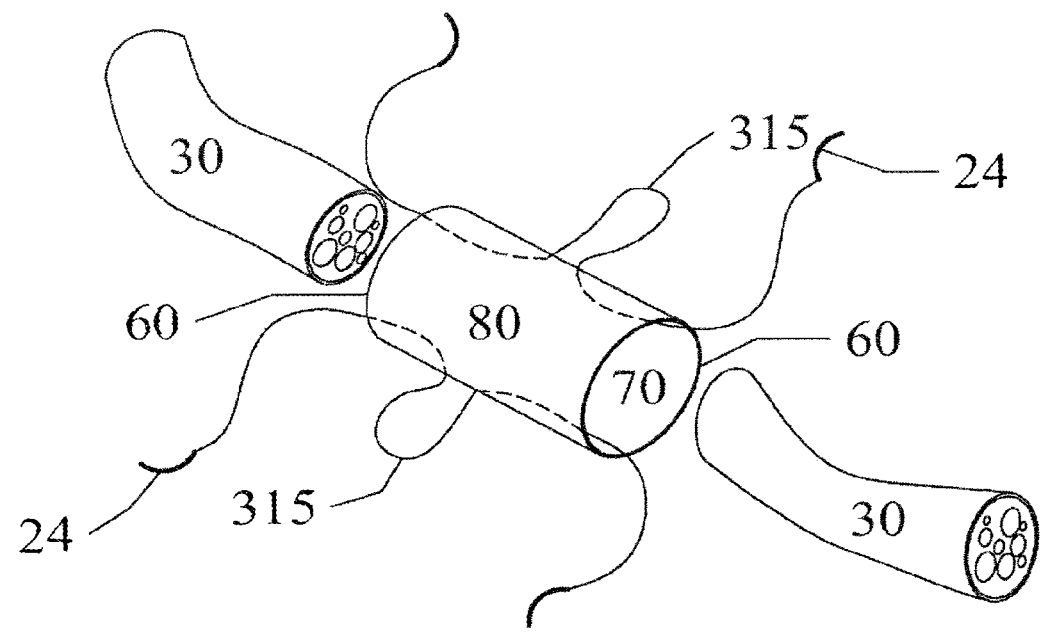
FIG. 12 is an illustration of the multi-pulley system for a nerve sleeve, as shown in FIG. 11, with two nerve ends emplaced for attachment to the sutures.
Figure 13:
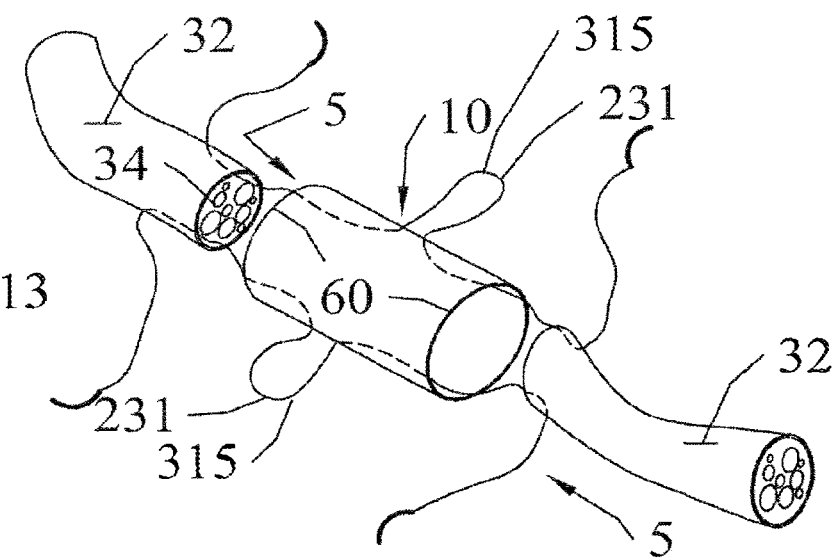
FIG. 13 is an illustration of the multi-pulley system for a nerve sleeve, as shown in FIG. 12, with the two nerve ends attached to the pulley system.
Figure 14:
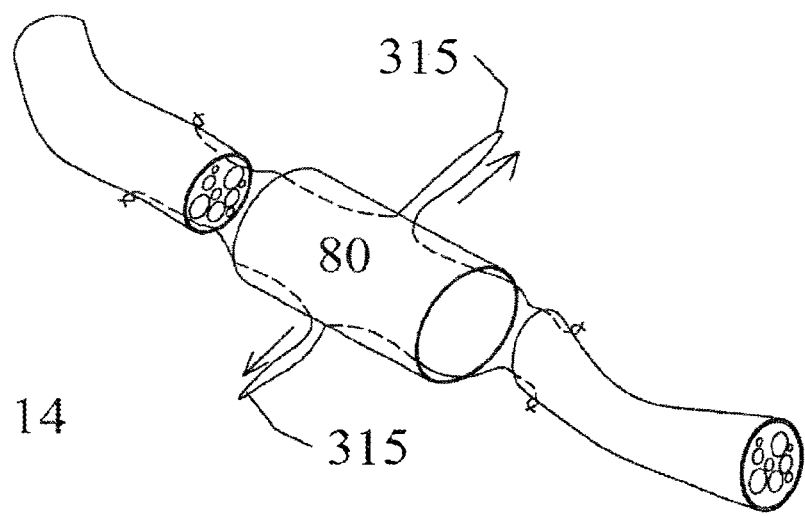
FIG. 14 is an illustration of the multi-pulley system for a nerve sleeve, as shown in FIG. 13, where the tags sutured through the nerve ends have been cut and knotted and the pulley loop is beginning to draw the nerve ends into the apertures at either end of the nerve sleeve.
Figure 15:
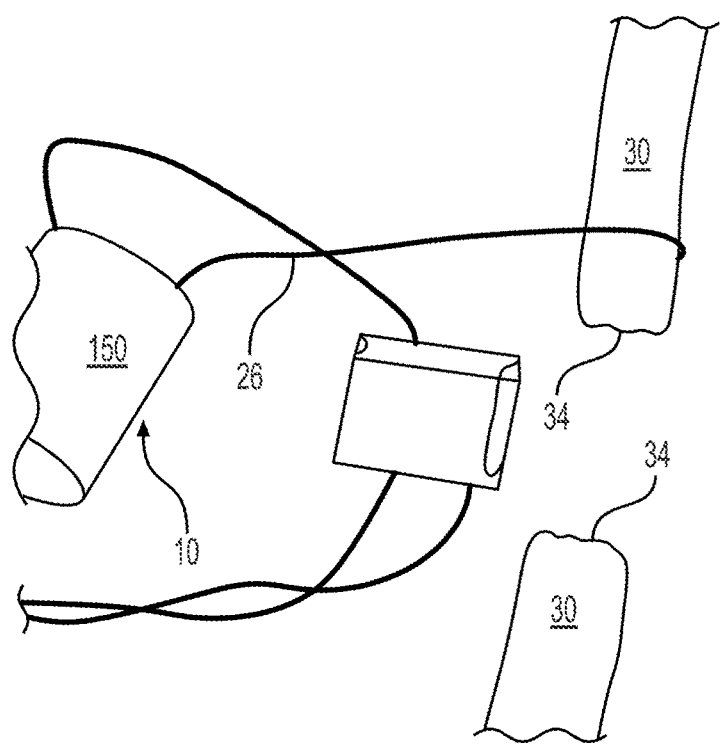
FIG. 15 is a photograph showing the sutures of a multi-pulley system for a nerve sleeve being attached to a nerve end. In this photograph, one tag end of a suture has been attached to the nerve end.
Figure 16:
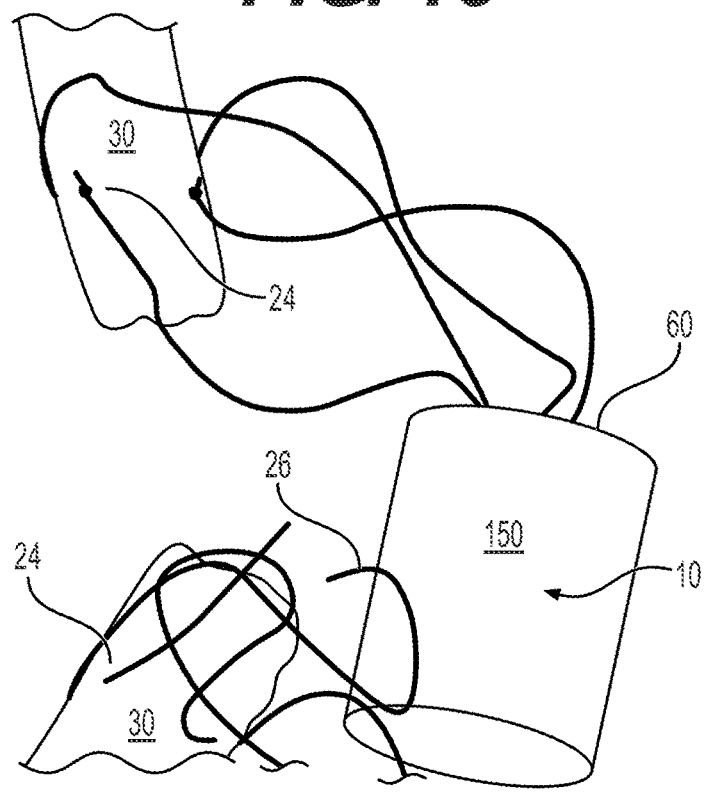
FIG. 16 is a photograph showing the sutures of a multi-pulley system for a nerve sleeve attached to a nerve end. In this photograph, all of the suture tags have been attached to the nerve end and are also shown going through the wall of the implant.
Figure 18:
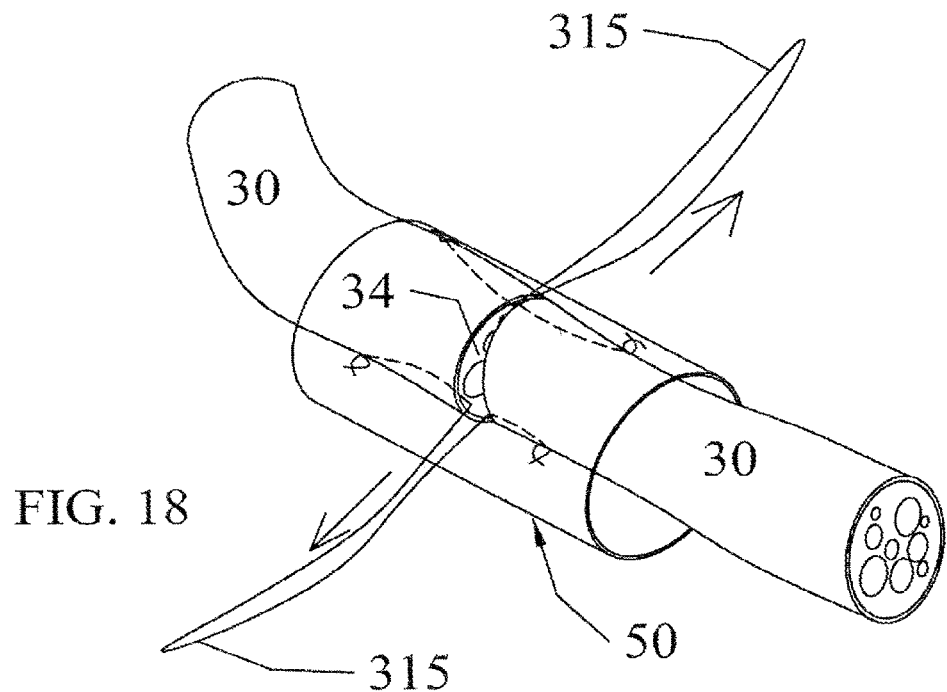
FIG. 18 illustrates a multi-pulley system, such as shown in FIG. 17, drawing two nerve ends into either end aperture of a nerve sleeve by pulling on the pulley loop on the outside of the wall.
Figure 19:
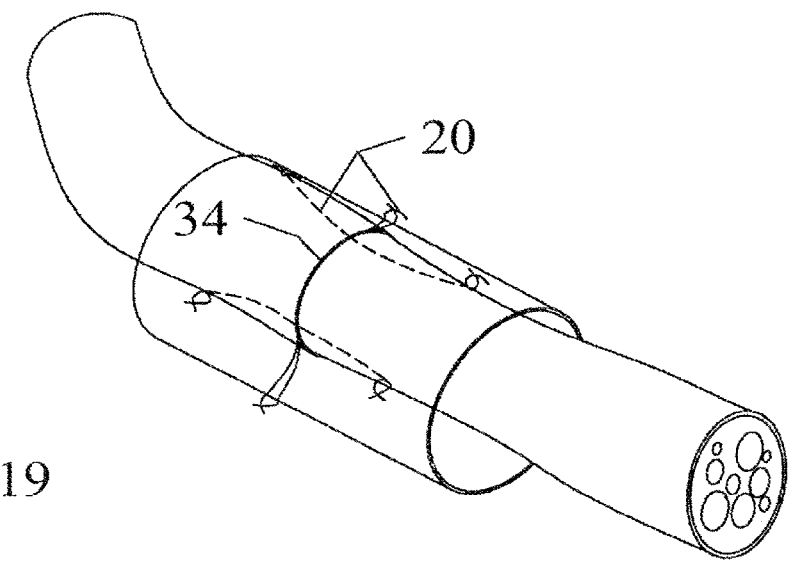
FIG. 19 illustrates the multi-pulley system of FIG. 18 where the nerve ends have been completely drawn into the nerve sleeve and are adjusted to be sufficiently close that the nerve faces just touch without being crushed together. The pulley loop has also been cut and tied off on the outside of the nerve sleeve wall.

A pulley loop can be advantageous because it can not only inhibit the suture ends from being pulled through the wall 80 into the bore 70, thus dismantling the pulley system 200, but also allows the surgeon to pull on one point 231 to draw two nerve ends into the sleeve implant. This can be achieved with a single suture line forming a pulley loop 230 and each end extending out of one of each of the apertures. Ideally, there are two or more dual needle end sutures configured in the wall with pulley loops, an example of which is shown in FIG. 12. A surgeon can attach the two suture ends extending from each open end 5 to a nerve at each end of the sleeve implant 150, as shown in FIGS. 13, 16, and 17. After removing the needle and tying off the suture ends, the surgeon can then pull on each pulley loop 230 to take up the slack in the suture and bring the nerve faces into alignment with the respective apertures. By continuing to pull on the two or more pulley loops, the face ends 34 of the two nerves can be drawn into the opposing sleeve implant apertures at each open end, which is shown, for example, in FIGS. 18 and 20. Once the faces have been adequately coapted by ensuring that they are in contact, but not crushed or pressed too firmly against each other, the pulley loops can be cut and tied off to secure the nerve ends within the sleeve implant. One example of this is shown in FIG. 19. If necessary or desirable, additional sutures can be used to secure the nerve ends and the sleeve implant.

Figure 20:
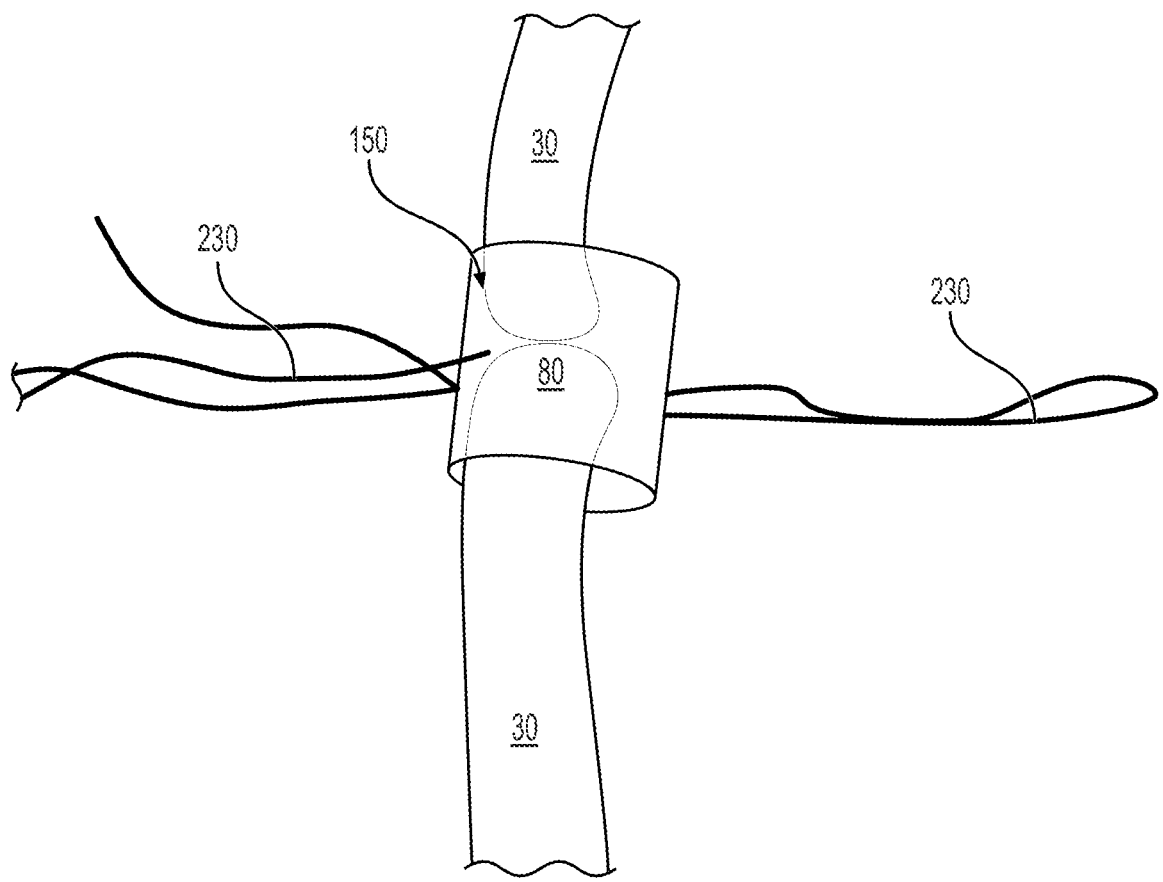
FIG. 20 is a photograph showing the multi-pulley system of FIG. 19 where the nerve ends have been completely drawn into the nerve sleeve and are adjusted so that the faces of the nerve ends just touch. For the purposes of illustration, the nerve sleeve is larger than required, being approximately 10 mm in diameter with a nerve of approximately 6 mm in diameter.
Figure 21:
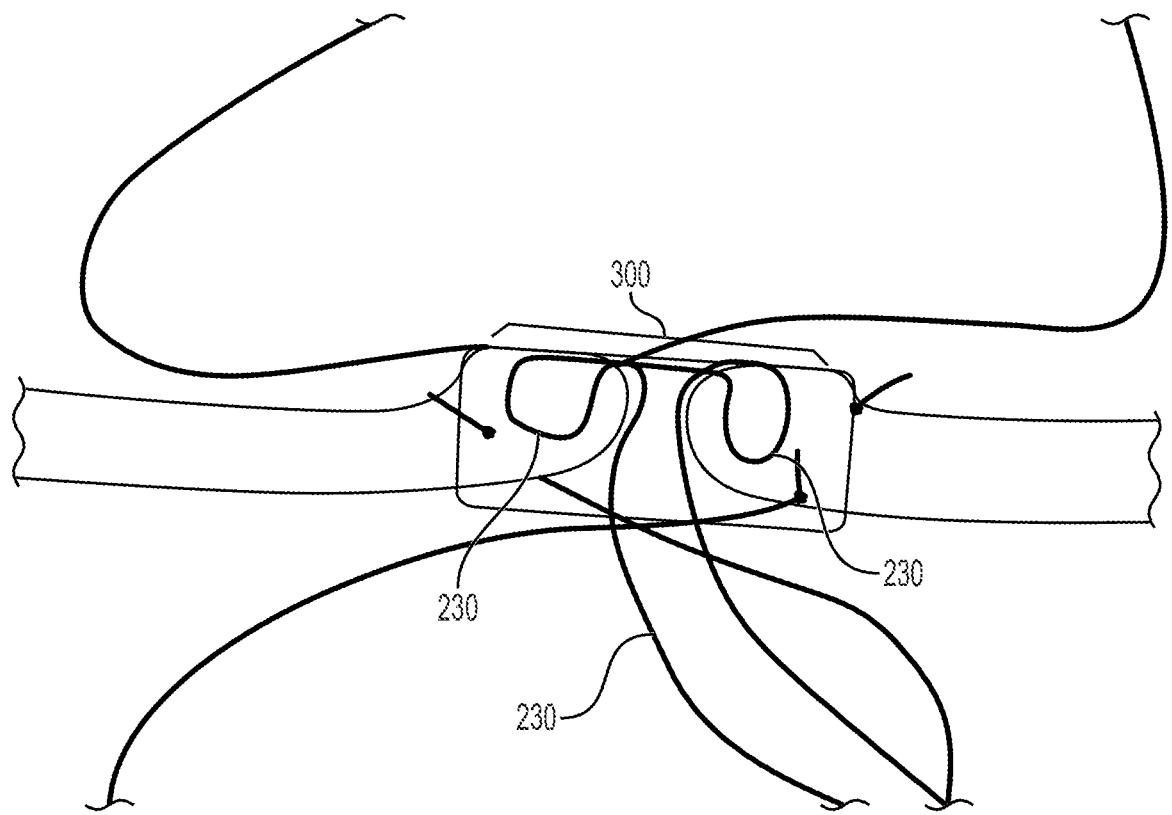
FIG. 21 is a photograph showing a multi-pulley system, such as shown in FIG. 19, as well as a cinching loop incorporated with the nerve sleeve. In this photograph, the nerve ends have already been drawn into the nerve sleeve using the tags of the pulley system. The noose knot has not yet been utilized and is shown by the loose looping of the suture within the nerve sleeve.
Figure 22:
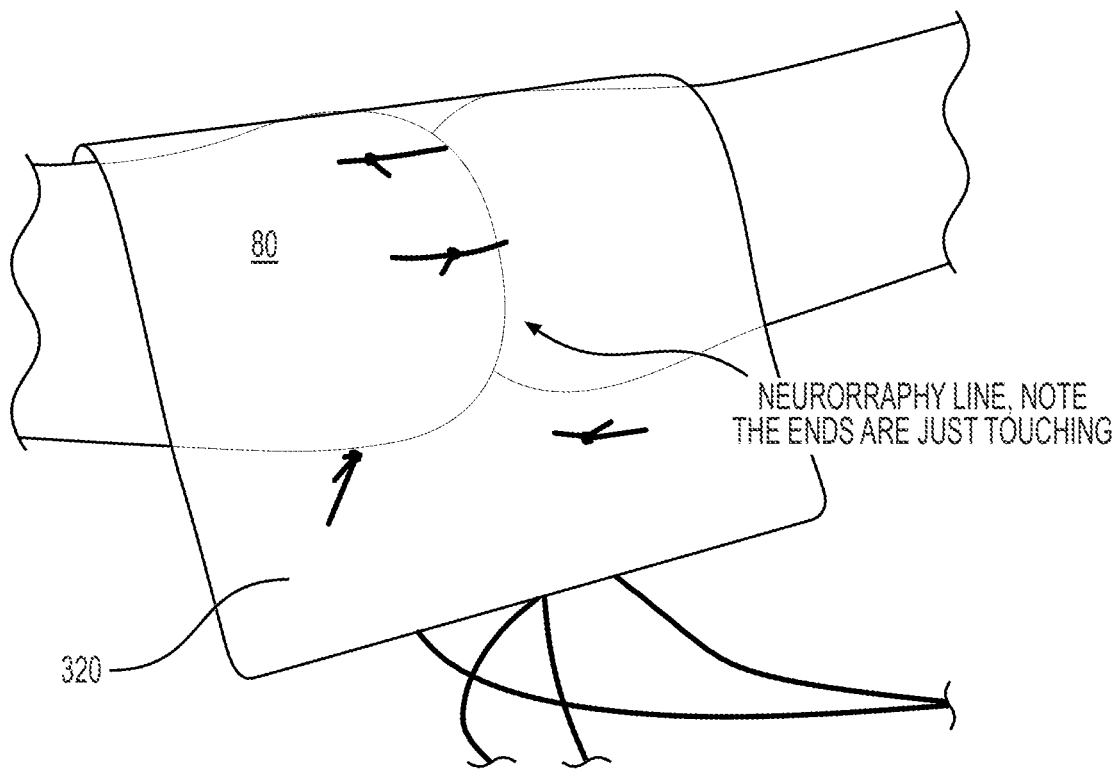
FIG. 22 is a photograph showing the multi-pulley system of FIG. 20, where the tags have been pulled tight, cut, and tied off to secure the nerve ends within the nerve sleeve. Manual noose knots of a cinching loop system has also been utilized to create a pucker seen towards the bottom of the photograph. Note that the suture line seen at the bottom of the image is the untied pulley for the opposite side.
Figure 23:
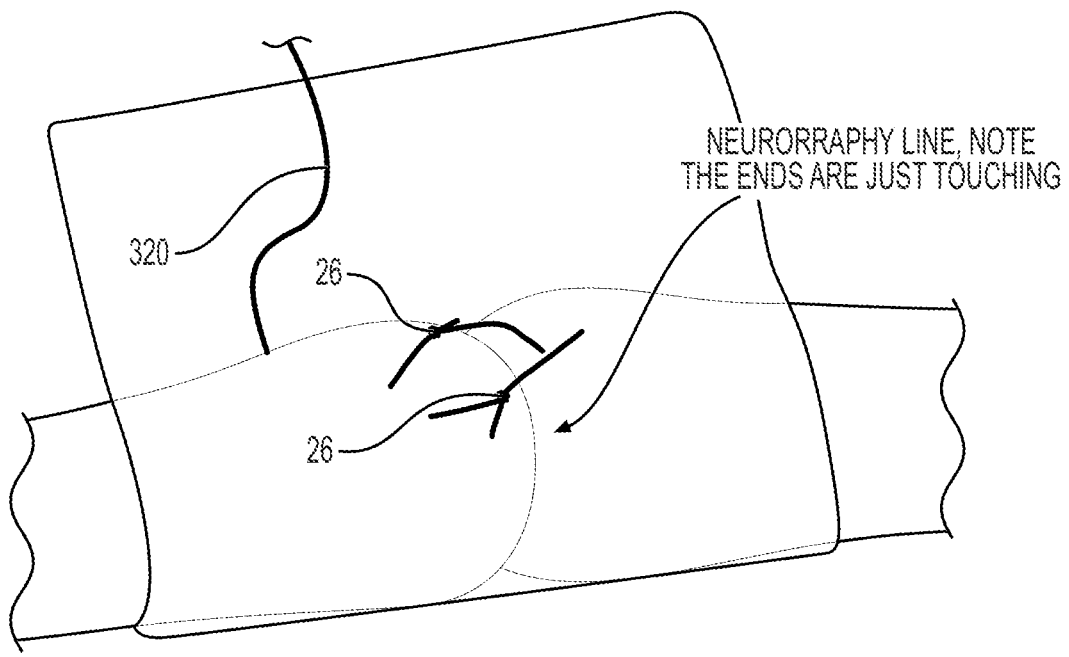
FIG. 23 is a photograph showing the multi-pulley system of FIG. 22 with all pulleys secured.

Oftentimes it can be helpful to use an implant 50 that is overly large for the diameter of the nerve or nerves being covered or coapted. This can make it easier to draw a nerve end into the open end 5 of an implant with minimal or no further damage to the nerve face 34. However, this can leave a larger aperture 60 than desired after the nerve is emplaced and the implant may not provide sufficient protection for the nerve or nerves. One non-limiting example of this is shown in FIG. 20, where the diameter (D) of the sleeve is noticably larger than the circumference of the nerve. In this situation, it can be helpful for the diameter of the implant and/or the aperture to be reduced or tightened around the nerve to protect the neurorraphy line and facilitate healing.

Figure 5A:
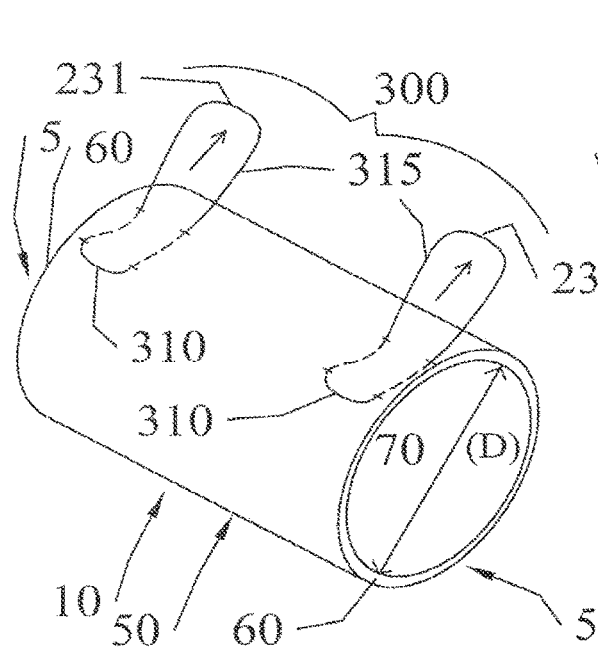
FIGS. 5A and 5B illustrate embodiments of cinching pulley systems that can be used to decrease the size of the aperture and/or the diameter (D) of a sheathing implant, so that it can conform to the shape and size of one or more nerve ends therein.

One embodiment of the subject invention is a cinching loop 300 by which either or both the aperture and the implant diameter can be reduced after a nerve or nerves are emplaced therein. This embodiment utilizes a suture line stitched through the implant 50, so that it crosses the bore 70 at least once, ideally at least twice, and goes through the wall of the implant 50 in two, ideally four, locations—where it goes into the bore and where it comes out of the bore. Where the suture line passes through the bore once, one end can be secured or anchored. Alternatively, where the suture line passes through the bore twice, a stitch 310 can be formed on the outside of the wall, which can secure the suture line. When the ends are tied or otherwise secured together, the suture forms a continuous loop through the implant wall with a noose knot 315 on the outside of the wall and the stitch 310 on the other side of the wall, an example of which is shown in FIG. 5A. This allows the cinching loop 300 to be pulled at one point 231 to draw the sides of the wall together at two places at either end of the stitch. This forms a pucker 320 at that point above the wall where the wall is drawn together and reduces the diameter (D) of the implant. If the cinching loop is near an aperture 60, such as shown in FIG. 5A, pulling the noose knot 315 will cause the stitch to tighten against the wall and can reduce the diameter of the implant at or near the aperture. The circular or continuous loop of the suture advantageously inhibits removal of the cinching loop from the implant.

Figure 5B:
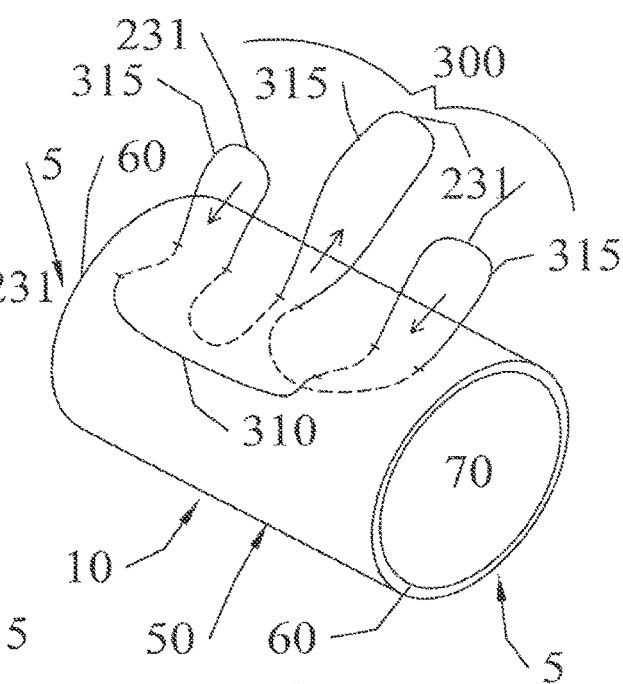
Figure 6:
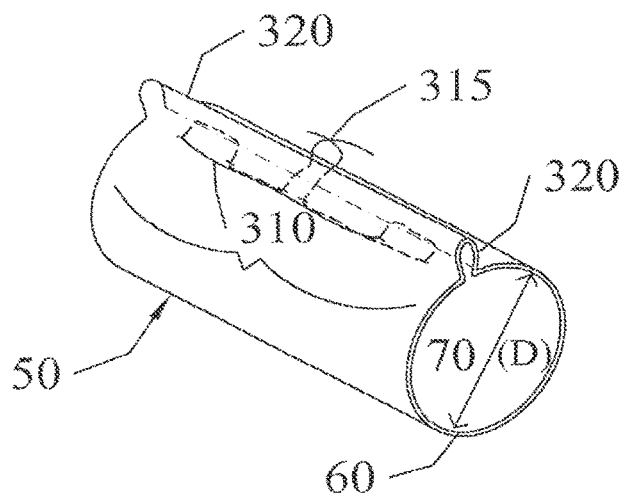
FIG. 6 illustrates how the configuration of the threaded suture line in FIG. 5B allows the cinching loop to be used to tighten the suture line, drawing a portion of the wall of the implant together, to create a partitioned area or pucker, which reduces the diameter (D) of the aperture and, as seen here, the diameter of the entire bore.
Figure 7:
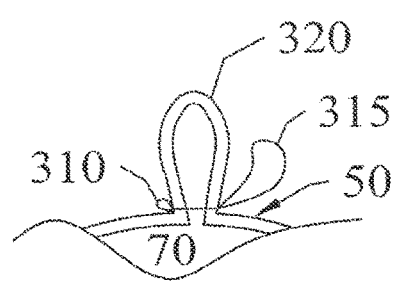
FIG. 7 illustrates an enlarged, end view of a portion of a sheathing implant having a cinching loop system. This illustration shows the pucker formed on one side of the implant wall when the suture is pulled tight to draw a part of the wall together to create the pucker.
Figure 8:
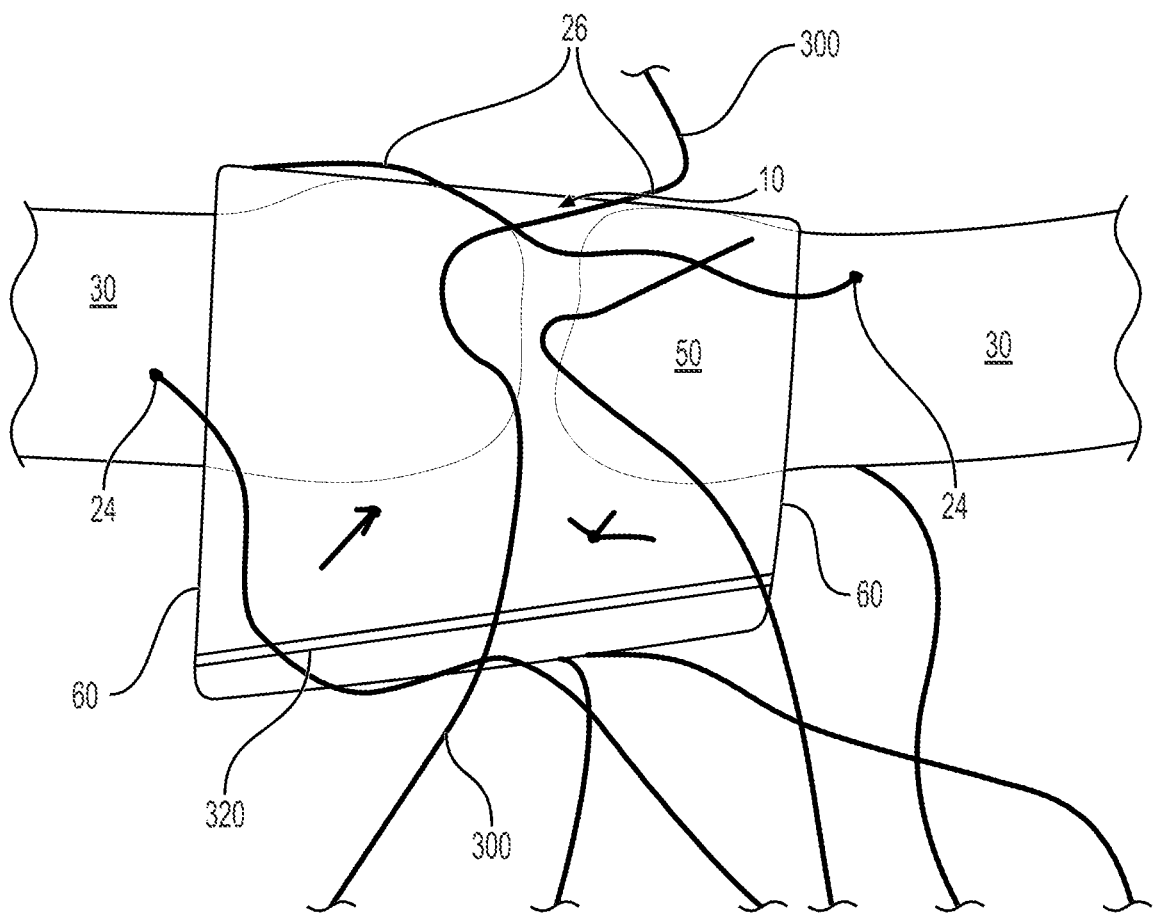
FIG. 8 is a photograph of two nerve ends that have been drawn into a nerve sleeve sheathing implant utilizing a suture pulley system and a cinching loop to conform the nerve sleeve around the two nerve ends. In this photograph there is shown a pulley system as shown in FIG. 1, where a single suture is used on two sides of the nerve.

Alternatively, the suture line of a cinching loop can pass through the bore four times, so as to provide at least one stitch 310 on the outside of the wall and at least two noose knots 315 opposite to the stitch and on the outside of the implant wall 80, where one noose knot can be pulled to tighten the entire cinching loop system to create a wall pucker 320. In a particular embodiment, the suture is threaded through the bore to provide at least three noose knots on the outside of the implant wall, where at least one is near to an open end 5. One example of this multiple noose knot system is shown in FIGS. 5B and 6. In this example, there is a single stitch 310 on the outside of the wall. When one of the multiple noose knots is pulled away from the wall of the implant 50, for example, a noose knot near a closed end 10 or cent or the sleeve implant 50, it causes the wall to come together at all of the points where the suture thread goes through the wall on either side of the bore, which is shown, by way of example, in FIG. 7. When the cinching loop is drawn tight, there will be formed a pucker 320 above the wall of the implant, formed by that part of the wall that was pulled together, one example of which is shown in FIGS. 6 and 8. In a particular embodiment, the threading of the suture forms a noose knot near at least one aperture 60 and at least one other noose knot between the aperture and the closed end. This can reduce the diameter of both the aperture and the bore. If more than two apertures are present, a noose knot can be fainted near each, as shown, for example, in FIG. 6. In practice, any one or more of these noose knots can be pulled to tighten the entire cinching loop and form the pucker 320.

Figure 9:
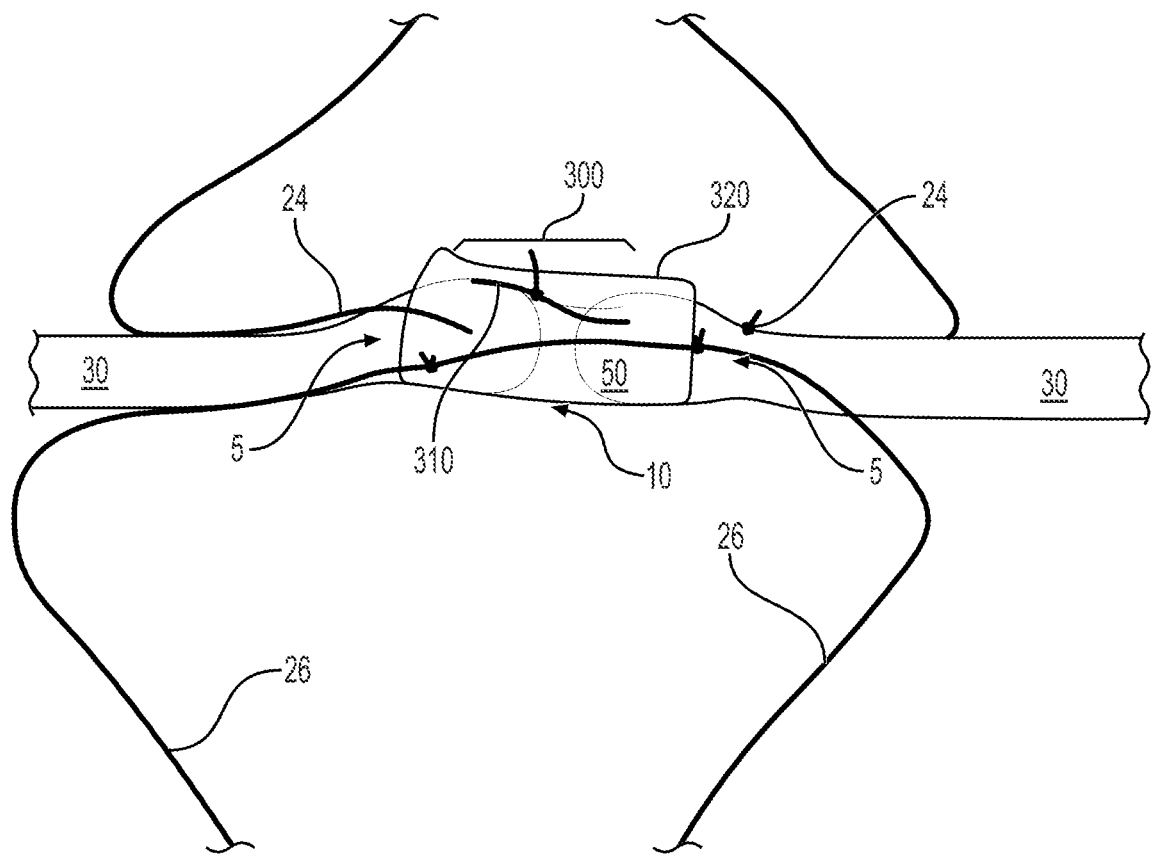
FIG. 9 is a photograph of two ends that have been drawn into a nerve sleeve utilizing a suture pulley system and a cinching loop to conform the nerve sleeve around the two nerve ends. In this photograph, it can be seen how the cinching loop can be tied off, once the pucker is created.
Figure 10A:
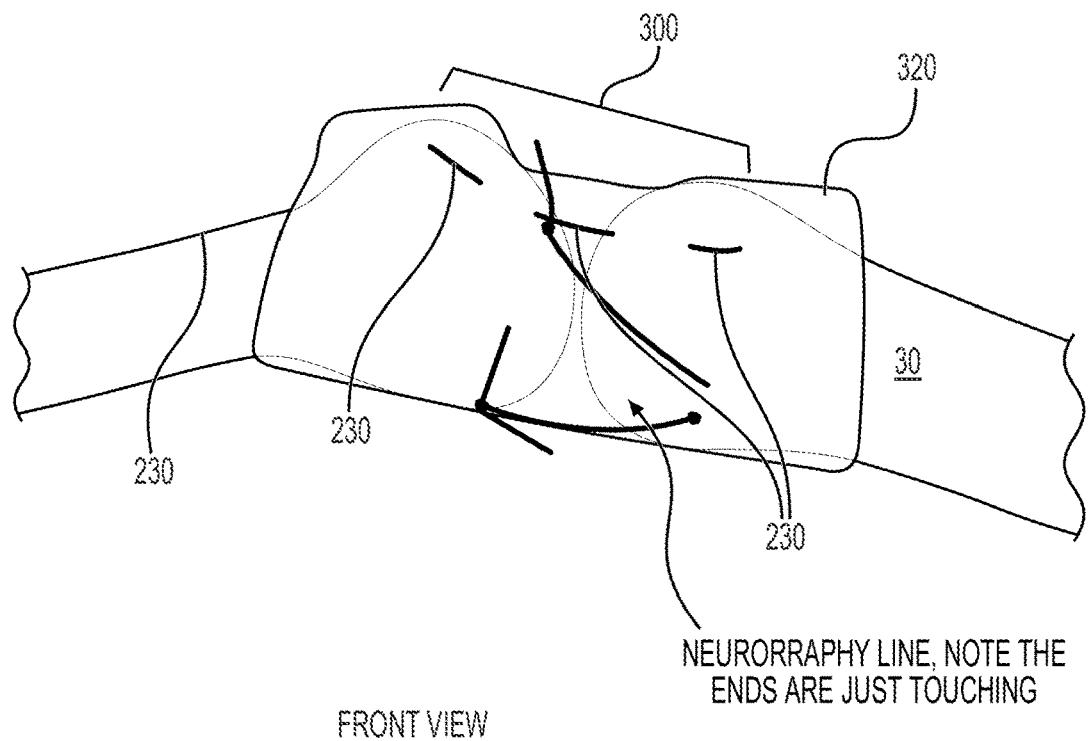
FIGS. 10A and 10B are enlarged front views and back views, respectively, of the nerve shown in FIG. 9. The front and back views shows how the pulley loops can be cut and tied off after the nerve ends are drawn into the tube and opposed to each other.
Figure 10B:
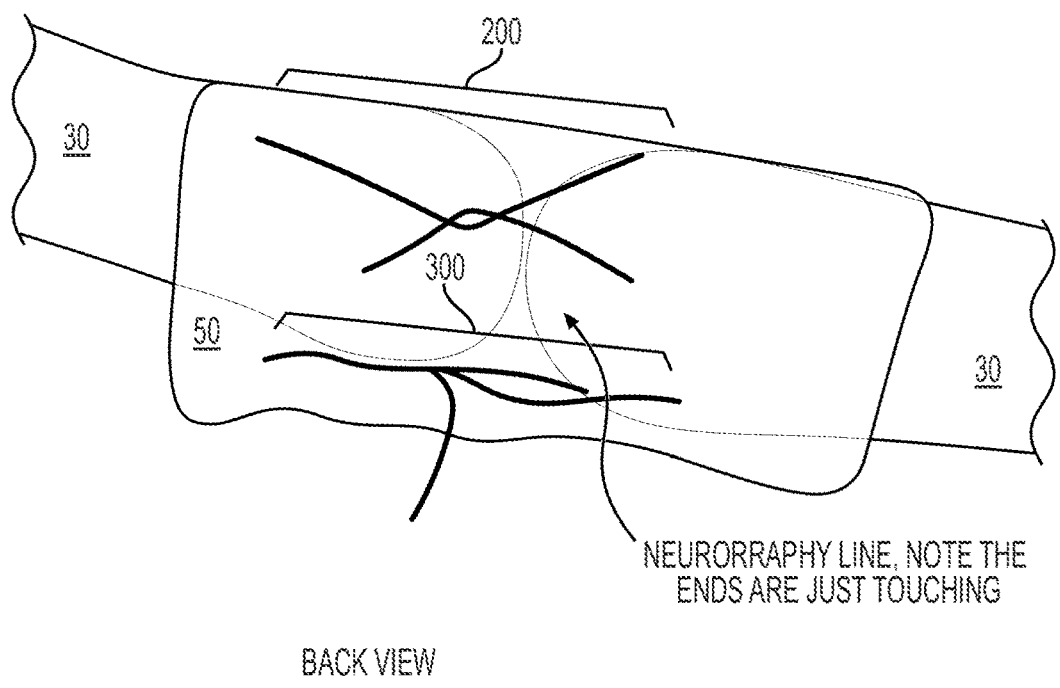

Once the noose knot 315 of the one or more cinching loops 300 have been pulled and the sleeve implant wall tightened around the one or more nerve faces 34 being sheathed, the knots can be cut and tied off on the outside of the implant to hold the nerve ends and nerve sheath in position 320. Excess suture line can also be removed. Examples of this are shown in FIGS. 9, 10A and 10B where it can be seen that the suture has been drawn tight against the implant to form the pucker 320 and the ends of the noose knots have been tied.

There can be multiple variations of a cinching loop where there are noose knots in specific locations on an implant to allow for strategic tightening of an implant. There can be more than one cinching loop on an implant, such that an implant could be tightened separately at different locations, such as the embodiment shown in FIG. 5A. In addition, while the embodiments described above provide a continuous loop system, variations can have a single suture line passing through the bore one time and going through the wall only twice. With this embodiment, each tag end 26 of the suture can be secured by an anchor 28 or knot to inhibit accidental dismantling of the cinching loop. The opposite or needle end can be pulled to draw the wall together at two points where the suture traverses the wall. While this embodiment is not shown in the attached figures, it is within the skill of a person trained in the art, who has benefit of this disclosure and the figures herein, to configure such a suture arrangement. Variations in the number of cinching loops, stitches, or noose knots on an implant, which provide the same function, in substantially the same way, providing substantially the same result are within the scope of this invention.

It is also possible for a pulley system 200, described in detail above, to be used on an implant 50 with a cinching loop 300. This can be advantageous as it would allow a larger diameter implant to be used with the pulley system and allow the implant to be tightened around the nerve afterwards. For example, in FIGS. 8 and 20, where an implant is significantly larger than the nerve ends therein, a cinching loop can be used in conjunction with the pulley system thereon to tighten the implant around the nerve, protecting the neurorraphy line and promoting healing.

While the embodiments described heretofore provide implants that can be pre-set with one or more pulley systems and/or cinching loop systems, the methods described herein could be practiced using implants that are not pre-set with such systems. Sutures are currently used to secure implants to nerves. The methods described herein could be used to create a pre-set implant just prior to surgery utilizing currently known and used sutures. A suture could be used intraoperatively to create pulley loops on an implant as needed by passing the needle of the suture through the implant. Still further, an implant pre-set with one type of system could be selected for use in a patient and then modified pre-surgically or intraoperatively with sutures to include additional suture motifs, either pulley sutures or cinching sutures. By way of non-limiting example, an implant pre-set with a pulley system could be used to coapt nerves within an implant. After coaptation, sutures could be used to create a cinching loop on the implant to tighten the implant around the coapted nerves.

It can be critical that nerve repair after an injury be done quickly and accurately to promote proper healing. Whether it is coaptation of severed nerve ends or capping a nerve end that will not be rejoined, implants are commonly used to facilitate the procedures. The embodiments and methods of subject invention provide implants that have the potential to improve the speed and accuracy at which nerves are repaired. By providing a pulley system on the implant, nerve ends can be quickly drawn into an implant with less prodding and manipulation of the nerve. The cinching systems described herein provide an opportunity to use larger sized implants that can make for easier, less traumatic placement of the nerve and allow the implant to be tightened around the nerve so that it still protects and separates the neurorraphy line from other surrounding tissues and fluids. The methods described herein provide the advantage of allowing a surgeon to utilize materials already used in the surgical suite to create the devices of the subject invention. While this is not an ideal situation, as it can take time and expertise to create a pulley or cinching loop on an implant, it provides an option when such implants are not available or their use was not anticipated.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

I claim:

1. A method, comprising:
   implanting an implant into a patient, wherein the implant comprises a wall that defines a bore having at least one aperture, and at least one pulley system pre-set into the wall before delivery of the implant into the patient, wherein the at least one pulley system includes a flexible strand having a tag end and a needle end;
   attaching a tissue to the needle end;
   pulling the tag end through the wall of the implant until the tissue attached to the needle end passes through the at least one aperture and into the bore of the implant; and
   securing the tag end outside the wall to inhibit movement of the tissue within the bore.

2. The method of claim 1, wherein the flexible strand traverses the wall so that the tag end extends out from the wall and the needle end passes through the bore and out of the at least one aperture before delivery of the implant into the patient.

3. The method of claim 1, wherein the implant comprises at least two apertures, and wherein the flexible strand includes at least two flexible strands having a tag end and a needle end, wherein the at least two flexible strands are pre-set into the wall before delivery of the implant into the patient so that the tag ends of the at least two flexible strands extend from the wall and each of the needle ends of the at least two flexible strands extends out of one of the at least two apertures.

4. The method of claim 3, further comprising making the implant tubular.

5. The method of claim 3, wherein the step of attaching the tissue to the needle end includes attaching tissue to the needle end of each of the at least two flexible strands;
   wherein the method further comprises removing a needle from the needle end of each of the at least two flexible strands; and
   wherein the step of pulling the tag end through the wall of the implant until the tissue attached to the needle end passes through the at least one aperture and into the bore of the implant includes pulling each tag end of the at least two flexible strands through the wall of the implant until tissue attached to each needle end passes through one of the at least two apertures and into the bore of the implant.

6. The method of claim 5, wherein the step of securing the tag end outside the wall to inhibit movement of the tissue within the bore includes securing each tag end of the at least two flexible strands to inhibit movement of tissue within the bore.

7. The method of claim 1, wherein the implant comprises two apertures, wherein the flexible strand includes at least two flexible strands having a tag end and a needle end, wherein the at least two flexible strands are pre-set into the wall before delivery of the implant into the patient so that the tag ends of each of the at least two flexible strands extend from the wall and the needle ends of each of the at least two flexible strands extend out of each aperture, and wherein the tag ends of the at least two flexible strands form a pulley loop that extends from the wall.

8. The method of claim 1, wherein the tissue attached to the needle end is a nerve tissue, and wherein the step of pulling the tag end through the wall of the implant until the tissue attached to the needle end passes through the at least one aperture and into the bore of the implant pulls an end of the nerve tissue through the at least one aperture and into the bore of the implant.

9. An implant comprising:
a wall that defines a bore having at least one aperture, wherein the wall has a length, and wherein the at least one aperture is configured to receive at least a portion of a tissue;
a cinching system pre-set into the wall before delivery of the implant into a patient, wherein the cinching system comprises:
at least one flexible strand having at least one tag end, wherein a first flexible strand of the at least one flexible strand traverses a first region of the wall in at least two locations so that the first flexible strand crosses into the bore of the implant at least twice and forms a stitch along an exterior of the wall and along a portion of the length of the wall, and wherein the first flexible strand traverses a second region of the wall in at least two locations, such that the at least one tag end extends through the wall to an exterior of the implant, wherein the second region is spaced apart from the first region in a direction generally perpendicular to the length of the wall.

10. The implant of claim 9, wherein the at least one tag end includes two tag ends, and wherein the two tag ends are secured together external to the implant.

11. The implant of claim 9, wherein the at least one tag end includes two tag ends, and wherein the two tag ends are connected to form a noose knot external to the implant.

12. The implant of claim 9, wherein the first flexible strand traverses the second region of the wall in at least two locations, so that at least one noose knot is formed external to the second region of the wall, and wherein the first flexible strand is located proximate to a first aperture of the at least one aperture of the implant.

13. The implant of claim 12, wherein the implant has an end opposite the first aperture;
wherein the at least one flexible strand further includes a second flexible strand located proximate to the end opposite the first aperture, and wherein the end is either closed or has a second aperture; and
wherein the second flexible strand traverses a third region of the wall in at least two locations so that the second flexible strand crosses into the bore of the implant at least twice and forms a second stitch along the exterior of the wall and along a portion of the length of the wall, and wherein the second flexible strand traverses a fourth region of the wall in at least two locations, such that at least one tag end of the second flexible strand extends through the wall to the exterior of the implant, and forms at least one other noose knot external to the fourth region of the wall, and wherein the fourth region is spaced apart from the third region in a direction generally perpendicular to the length of the wall.

14. The implant of claim 9, wherein the first flexible strand traverses the second region of the wall in at least six locations, so that a plurality of tag ends extend external to the second region of the wall, and wherein at least one pair of the plurality of tag ends are coupled together to form one or more noose knots external to the second region of the wall.

15. The implant of claim 9, wherein pulling the at least one tag end of the first flexible strand pulls the first region and the second region of the wall closer to each other to form a puckering of the wall to reduce a size of the bore.

16. The implant of claim 9, wherein the implant is formed of a biomaterial that comprises one of more of high density polyethylene; polyethylene glycol hydrogel; purified proteins from one or more of human, animal, plant, fungus, bacterial, and synthetic sources; or decellularized tissue constructs.

17. The implant of claim 9, wherein the implant has been made tubular.

18. The implant of claim 17, wherein the implant has been pre-rolled.

19. The implant of claim 17, wherein the implant has two apertures.

20. The implant of claim 9, wherein the implant is tubular.

21. The implant of claim 9, wherein the implant has one aperture and a closed end opposite the one aperture.

22. A method, comprising:
implanting an implant into a patient, wherein the implant comprises:
a wall that defines a bore having at least one aperture, and wherein the wall has a length; and
a cinching system pre-set into the wall before delivery of the implant into the patient, wherein the cinching system comprises:
at least one flexible strand having at least one tag end, wherein a first flexible strand of the at least one flexible strand traverses a first region of the wall in at least two locations so that the first flexible strand crosses into the bore of the implant at least twice and forms a stitch along an exterior of the wall and along a portion of the length of the wall, and wherein the first flexible strand traverses a second region of the wall in at least two locations, such that the at least one tag end extends through the wall to an exterior of the implant, wherein the second region is spaced apart from the first region in a direction generally perpendicular to the length of the wall;
positioning tissue through one or more of the at least one apertures and within the implant;
pulling the at least one tag end of the first flexible strand so as to pull the first region and the second region of the wall closer to each other to form a puckering of the wall to reduce a size of the bore; and
securing the at least one tag end to secure the reduced size of the bore.

23. The method of claim 22, wherein the first flexible strand includes at least two tag ends that extend external to the implant;
wherein the method further includes connecting the at least two tag ends to form at least one noose knot external to the implant;
wherein the step of pulling the at least one tag end of the first flexible strand includes pulling the at least one noose knot so that the stitch pulls the first region and the second region closer to each other to form the puckering in the wall; and wherein the step of securing the at least one tag end to secure the reduced size of the bore includes securing the noose knot.

24. The method of claim 23, and wherein the first flexible strand is proximate to a first aperture of the at least one aperture of the implant.

25. The method of claim 24, wherein the implant has an end opposite the first aperture;

wherein the implant further comprises:
a second flexible strand located proximate to the end opposite the first aperture, and wherein the end is either closed or has a second aperture, wherein the second flexible strand traverses a third region of the wall in at least two locations so that the second flexible strand crosses into the bore of the implant at least twice and forms a second stitch along the exterior of the wall and along a portion of the length of the wall, and wherein the second flexible strand traverses a fourth region of the wall in at least two locations, such that at least one tag end of the second flexible strand extends through the wall to the exterior of the implant, and forms at least one other noose knot external to the fourth region of the wall, and wherein the fourth region is spaced apart from the third region in a direction generally perpendicular to the length of the wall;

wherein the method further comprises pulling the at least one other noose knot; and wherein the method further comprises securing the at least one other noose knot to secure the reduced size of the bore.

26. The method of claim 22, wherein the first flexible strand traverses the second region of the wall in at least six locations, so that a plurality of tag ends extend external to the second region of the wall, and wherein at least one pair of the plurality of tag ends are coupled together to form one or more noose knots external to the second region of the wall;

wherein the step of pulling the at least one tag end of the first flexible strand includes pulling at least one noose knot of the one or more noose knots; and wherein the step of securing the at least one tag end to secure the reduced size of the bore includes securing the at least one noose knot of the one or more noose knots.

27. The method of claim 22, wherein the tissue positioned within the implant through one or more of the at least one apertures is a nerve tissue.

28. The method of claim 22, further comprising making the implant tubular.

* * * * *